US010206621B2

(12) United States Patent
Zhang et al.

(10) Patent No.: US 10,206,621 B2
(45) Date of Patent: Feb. 19, 2019

(54) INSTRUMENTED WEARABLE DEVICE FOR MEASUREMENT OF PHYSIOLOGICAL PARAMETERS

(71) Applicants: Regents of the University of Minnesota, Minneapolis, MN (US); Mayo Foundation for Medical Education and Research, Rochester, MN (US)

(72) Inventors: Song Zhang, Lauderdale, MN (US); Rajesh Rajamani, Saint Paul, MN (US); Bruce Johnson, Rochester, MN (US)

(73) Assignees: Regents of the University of Minnesota, Minneapolis, MN (US); Mayo Foundation for Medical Education and Research, Rochester, MN (US)

( * ) Notice: Subject to any disclaimer, the term of this patent is extended or adjusted under 35 U.S.C. 154(b) by 167 days.

(21) Appl. No.: 15/240,731

(22) Filed: Aug. 18, 2016

(65) Prior Publication Data
US 2017/0049394 A1     Feb. 23, 2017

Related U.S. Application Data

(60) Provisional application No. 62/206,725, filed on Aug. 18, 2015.

(51) Int. Cl.
*A61B 5/00*     (2006.01)
*A61B 5/107*    (2006.01)
(Continued)

(52) U.S. Cl.
CPC .......... *A61B 5/6807* (2013.01); *A61B 5/0053* (2013.01); *A61B 5/1073* (2013.01);
(Continued)

(58) Field of Classification Search
CPC ...... A61B 2090/064; A61B 2562/0223; A61B 2562/0247; A61B 2562/164;
(Continued)

(56) References Cited

U.S. PATENT DOCUMENTS

2003/0193031 A1* 10/2003 Sathrum ........... H01J 37/32055
                                                            250/426
2015/0073717 A1*  3/2015 Hsu ...................... A61B 5/0803
                                                             702/19

OTHER PUBLICATIONS

S.S. Stuchley et al., "Permittivity Measurements at Microwave Frequencies Using Lumped Elements", IEEE Transactions on Instrumentation and Measurement, vol. IM-23, No. 1, Mar. 1974, pp. 56-62.

(Continued)

*Primary Examiner* — George Manuel
(74) *Attorney, Agent, or Firm* — Dicke, Billig & Czaja, PLLC

(57) ABSTRACT

This disclosure describes devices, system, and a method for the prediction and prevention of acute decompensated heart failure or other patient conditions involving fluid accumulation in legs or hands. In one example, a wearable device contains a drift-free leg-size sensor and a tissue-elasticity sensor. Both sensors may be relatively inexpensive and developed using innovative new sensing ideas. Preliminary tests with the sensor prototypes show promising results: the leg-size sensor is capable of measuring 1 mm changes in leg diameter and the tissue-elasticity sensor can detect 0.15 MPa differences in elasticity. In another example, a wearable system includes sensors for measuring a variety of physiological parameters, a processing module, and a communication module. A low-profile instrumented sock, e.g., a wearable device, with multiple sensors can provide an indication of heart failure status for a patient.

15 Claims, 16 Drawing Sheets

(51) Int. Cl.
*G06F 19/00* (2018.01)
*A61B 5/0205* (2006.01)
*A61B 5/024* (2006.01)
*A61B 90/00* (2016.01)

(52) U.S. Cl.
CPC ............ *A61B 5/4878* (2013.01); *G06F 19/00* (2013.01); *A61B 5/0205* (2013.01); *A61B 5/02405* (2013.01); *A61B 5/746* (2013.01); *A61B 2090/064* (2016.02); *A61B 2562/0223* (2013.01); *A61B 2562/0247* (2013.01); *A61B 2562/164* (2013.01)

(58) Field of Classification Search
CPC . A61B 5/0053; A61B 5/0205; A61B 5/02405; A61B 5/1073; A61B 5/4878; A61B 5/6807; A61B 5/746
See application file for complete search history.

(56) References Cited

OTHER PUBLICATIONS

H. Pin Kao et al., "Correlation of Permittivity and Water Content During Cerebral Edema", IEEE Transactions on Biomedical Engineering, vol. 46, No. 9, Sep. 1999, pp. 1121-1128.

I.S. Anand et al., "Design of the Multi-Sensor Monitoring in Congestive Heart Failure (MUSIC) Study: Prospective Trial to Assess the Utility of Continuous Wireless Physiologic Monitoring in Heart Failure", Journal of Cardiac Failure, vol. 17, No. 1, 2011, pp. 11-16.

S. Hadmani et al., "The application of a piezo-resistive cardiorespiratory sensor system in an automobile safety belt", Conference Proceedings Paper—Sensors and Applications, Int'l Electronic Conference on Sensors and Application, Jun. 1-16, 2014, pp. 1-6.

F.M. Merchant et al., "Implantable Sensors for Heart Failure", Circ Arrhythm Electrophysiol, Dec. 2010, pp. 657-667.

P.B. Adamson et al., "Continuous Autonomic Assessment in Patients with Symptomatic Heart Failure: Prognostic Value of Heart Rate Variability Measured by an Implanted Cardiac Resynchronization Device", Circulation, Oct. 19, 2004, pp. 2389-2394.

P. Peng et al., "Handheld Microtactile Sensor for Elasticity Measurement", IEEE Sensors Journal, vol. 11, No. 9, Sep. 2011, pp. 1935-1942.

D. Bertolini et al., "Time domain reflectometry to study the dielectric properties of liquids: Some problems and solutions", Rev. Sci. Instrum., vol. 61, No. 12, Dec. 1990, pp. 450-456.

J. Nuutinen et al., "Validation of a new dielectric device to assess changes of tissue water in skin and subcutaneous fat", Physiol. Meas., vol. 25, 2004, pp. 447-454.

L. Petaja et al., "Dielectric constant of skin and subcutaneous fat to assess fluid changes after cardiac surgery", Physiol. Meas., vol. 24, 2003, pp. 383-390.

E. Alanen et al., "Measurement of dielectric properties of subcutaneous fat with open-ended coaxial sensors", Phys. Med. Biol., vol. 43, 1998, pp. 475-485.

* cited by examiner

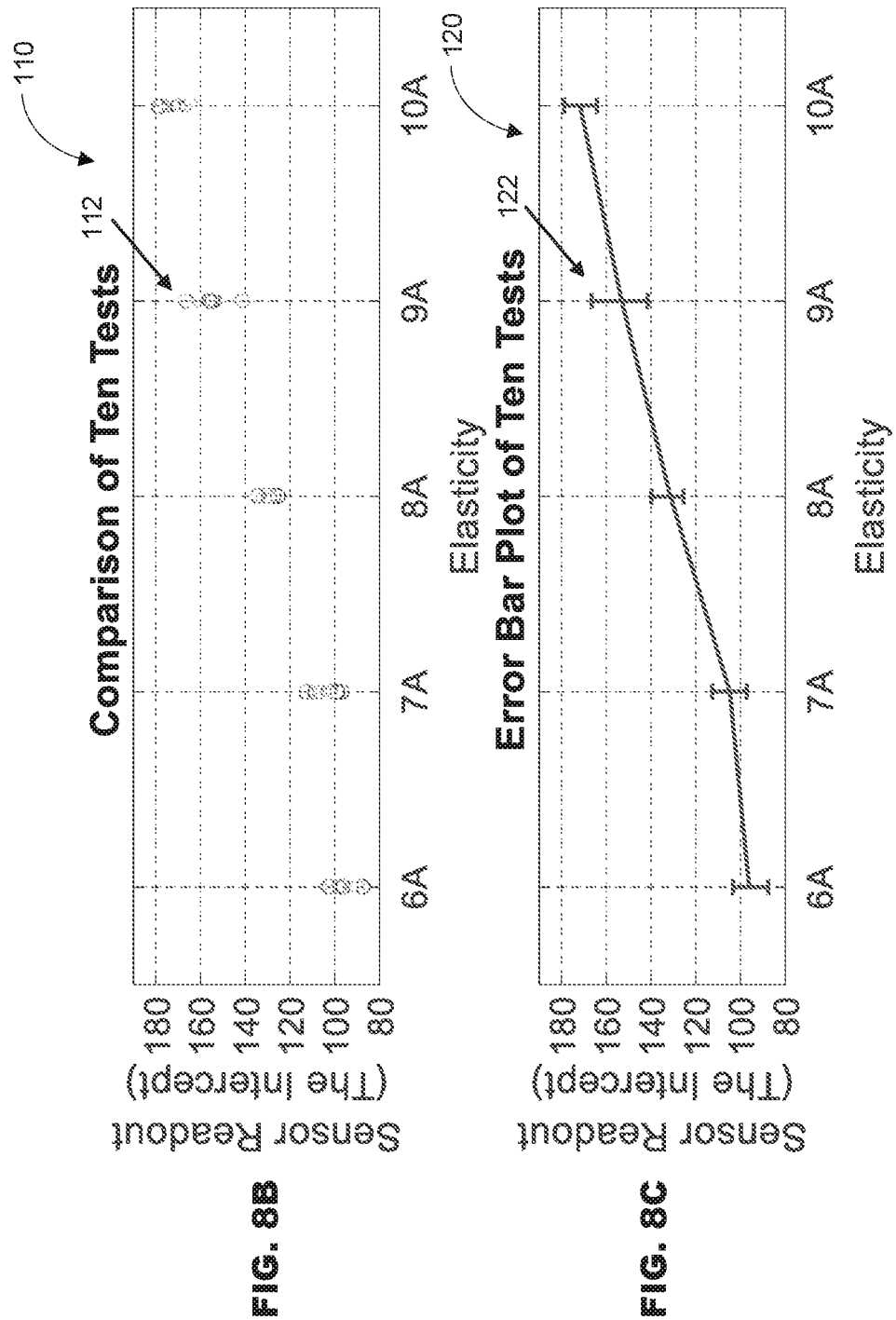

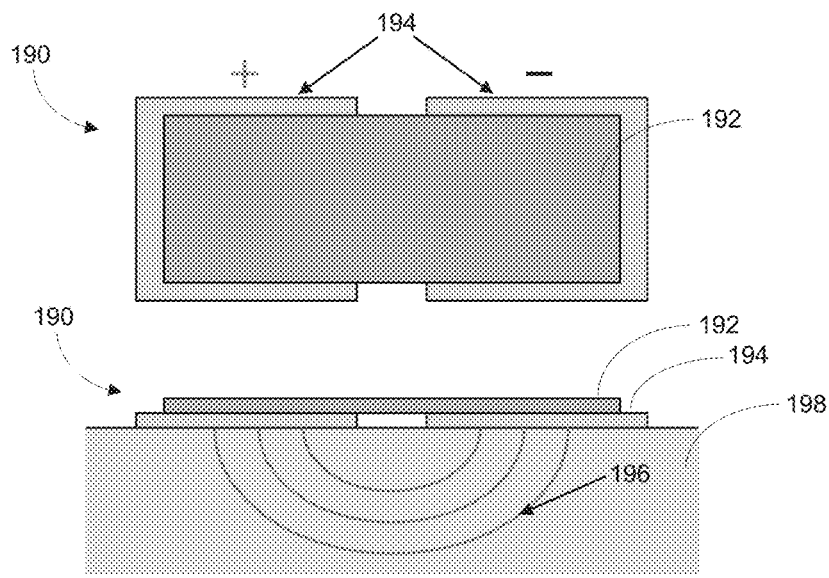
FIG. 13A
FIG. 13B
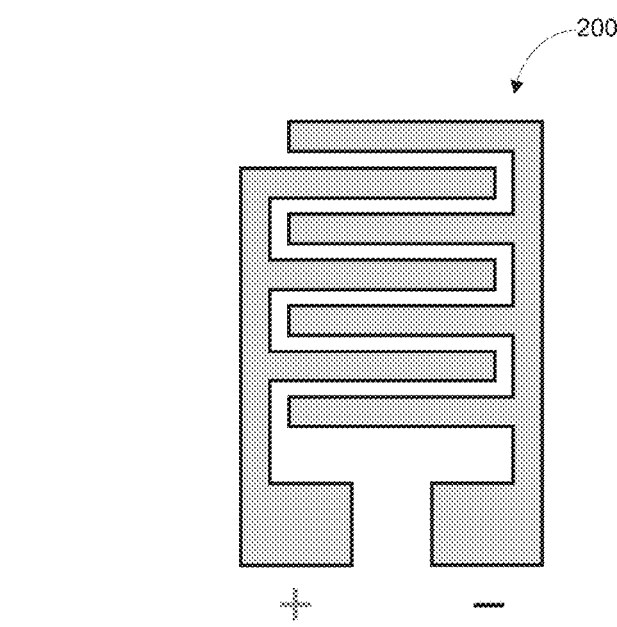
FIG. 14

INSTRUMENTED WEARABLE DEVICE FOR MEASUREMENT OF PHYSIOLOGICAL PARAMETERS

CROSS-REFERENCE TO RELATED APPLICATIONS

This Non-Provisional patent application claims the benefit of the filing date of U.S. Provisional Patent Application Ser. No. 62/206,725, filed Aug. 18, 2015, entitled "INSTRUMENTED WEARABLE DEVICE FOR MEASUREMENT OF PHYSIOLOGICAL PARAMETERS," which is herein incorporated by reference.

GOVERNMENT SUPPORT CLAUSE

This invention was made with government support under U.S. Pat. No. 1,231,582 awarded by the National Science Foundation. The government has certain rights in the invention.

TECHNICAL FIELD

This disclosure relates to systems and methods for physiological monitoring, and more specifically, external wearable sensors for detecting physiological parameters of a patient.

BACKGROUND

For 2011 to 2012, the annual total costs of cardiovascular disease in the United States were estimated to be $316.6 billion. Factors that continue to drive the prevalence of cardiovascular disease include advanced age, in addition to rising rates of obesity, diabetes, and heart-attack survival. Despite recent advances in medical treatment options, heart failure remains a leading cause of hospitalization in people over the age of 65. In some patients, chronic stable heart failure may easily decompensate, resulting in patient hospitalization or even mortality. Recurrent hospitalizations stemming from acute decompensated heart failure (ADHF) events result in significant patient mortality and health-care costs.

SUMMARY

Physiological changes that can occur in heart failure patients preceding an ADHF event, or with other patient conditions, include, for example, a gradual increase in total body water content, edema of the lower extremities, altered tissue elasticity, and alterations in autonomic function (e.g., alterations in heart rate variability). This disclosure describes example methods, devices, and systems that generally include wearable sensors capable of measuring various physiological parameters that may be indicative of decompensated heart failure or other health concerns. In some examples, a sensor may measure a physiological parameter such as the circumference of a body part (e.g., the ankle or leg), wherein an increase in circumference may indicate the progression of edema in the lower extremities. In other examples, a sensor may measure the physiological parameter of the elasticity of the tissue, such as the tissue of a leg or other lower body part.

The system may include one or more of these sensors and/or additional sensors that measure other physiological parameters such as water content and heart rate variability. Example devices and systems herein may achieve the measurement of several physiological parameters associated with an ADHF event; e.g., both body-part circumference and tissue elasticity, and may determine a heart failure status for the patient based on monitoring one or more of these sensor outputs. Measurements may be achieved through the application of a cost-effective and non-invasive wearable device, such as a sock coupled to one or more sensors or instruments, that incorporates the various features of an example device or system described herein. Example systems and methods for wearable physiological monitoring described herein may help provide better patient outcomes for a variety of health concerns, including those related to cardiovascular disease and other conditions.

In one example, a system for measuring a dimension of a sample includes one or more magnetic sensors configured to detect a magnetic field; an electromagnet (an inductor) configured to produce the magnetic field detectable by one or more magnetic sensors; a controller module configured to control delivery of an electrical signal to the electromagnet (the inductor) and receive, from each of the one or more magnetic sensors, a respective signal indicative of the magnetic field; and a stretchable material, wherein the electromagnet (the inductor) and the one or more magnetic sensors are coupled to respective portions of the stretchable material.

In one example, a device configured to determine an elasticity of a sample includes a first member comprising a first portion configured to deform a first area of a sample; a second member comprising a second portion configured to deform a second area of the sample different from the first area, wherein application of an external force to the first member causes the first portion to extend further into the sample than the second portion; a first force sensor coupled to the first member and configured to sense a first force to the first portion during deformation of the first area of the sample; a second force sensor disposed between the first member and the second member and configured to sense a second force representative of contact between the first member and the second member when the second portion deforms the second area of the sample; and a controller module configured to detect, based on the first force and the second force, the elasticity of the sample.

In another example, a system for monitoring a physiological status of a patient includes a size sensor configured to measure changes to a size parameter of a limb of the patient; an elasticity sensor configured to measure changes to an elasticity parameter of a limb of the patient; a processing module comprising one or more circuits configured to determine, based on at least one of the size parameter or the elasticity, that a physiological parameter indicative of a physiological status exceeds a threshold value; and a communication module comprising one or more circuits configured to transmit an alert signal to a computing device for alerting a user of the exceeded threshold value.

In another example, a method for monitoring a physiological status of a patient includes measuring, by a size sensor, changes to a size parameter of a limb of the patient, measuring, by an elasticity sensor, changes to an elasticity of a tissue portion of the patient, determining, by a processing module and based on at least one of the size parameter or the elasticity, a physiological parameter indicative of the physiological status, determining, by the processing module, that the physiological parameter exceeds a threshold value, and transmitting, by a communication module, an alert signal to a computing device for alerting a user of the exceeded threshold value.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 8B is a graph illustrating the comparative results of a series of tests of an example tissue-elasticity sensor upon materials of varying elasticity.

FIG. 8C is a graph illustrating a monotonic trend of readouts from the elasticity sensors for different elasticity values for the tests results illustrated by the graph of FIG. 8B.

FIG. 13A is a top view of an example water-content sensor including planar adjacent electrodes.

FIG. 13B is a side view of an example water-content sensor including planar adjacent electrodes.

FIG. 14 is a conceptual view of a comb structure of electrodes used in an example water-content sensor.

DETAILED DESCRIPTION

Figure 1A:
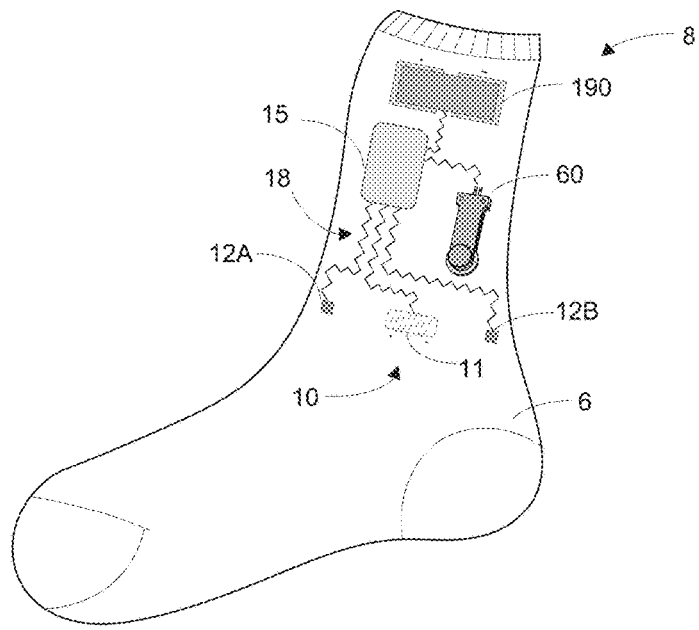
FIG. 1A is a conceptual illustration of an example wearable device, such as an instrumented sock, which includes a leg-size sensor, a tissue-elasticity sensor, a water-content sensor, and a wireless-enabled controller module.

This disclosure describes a system that may include one or more wearable sensors to provide monitoring of one or more physiological parameters indicative of a patient condition, such as heart failure. There are known physiological changes that occur in heart failure (HF) patients preceding an acute decompensated heart failure (ADHF) event: a gradual increase in total body water, lower extremity edema, weight changes, reduced activity levels and alterations in autonomic function (e.g., heart rate variability). Typically, there are three major methods for prediction of ADHF event. Assessment of weight can be used as a surrogate of fluid retention, but this method lacks sensitivity and specificity. Adhesive skin devices attached to the upper thorax can be used for monitoring but are found uncomfortable to use among HF patients. Implantable cardiac devices can provide certain measurements, but such devices are too expensive and invasive to be accessible to most of the HF population.

As described herein, a system including one or more wearable devices may be relatively inexpensive and non-invasive solutions that can provide continuous home monitoring of fluid status and other related variables in order to reliably monitor and predict impending decompensation in HF patients. In some examples, an instrumented wearable device ("device") described herein includes at least one sensor configured to measure and sense changes to a respective physiological parameter, such as the circumference of a patient's body part or the elasticity of the patient's tissue. Where the circumference of a body part is to be sensed, the device may employ magnetic sensing to provide accurate drift-free measurements even where a static state of the body part prevents piezoelectric sensing. Systems including a device configured to sense the circumference of a body part may be employed in the monitoring of numerous patient health conditions, including a variety of conditions characterized by edema; for example, conditions such as pre-eclampsia, liver disease, kidney disease, lymphedema, and adverse drug reaction (ADR), as well as the heart failure or cardiovascular disease described herein. In other examples, measuring a dimension, such as the circumference of a body part, may be used to monitor inflammation prior to and/or after injury or surgical procedures. Where tissue elasticity is to be sensed, the device may employ a simple yet reliable sensor that is activated by a user pressing a button or lever. In this way, the device may provide a noninvasive and relatively low-cost option for the reliable prediction of impending decompensation in heart-failure patients or indication of other symptoms or conditions.

The use of magnetic sensing to detect changes in the circumference of a body part may provide more accurate, drift-free measurements when compared to the use of sensors that rely on piezoelectric effects. Specifically, the use of magnetic sensing may provide detection of absolute and dynamic size measurements, including circumstances in which the size of the body part remains static or changes very slowly. Furthermore, the use of magnetic sensing may allow a system to measure size reliably, even under the influence of environmental changes to the magnetic field. In addition, magnetic sensing is a relatively low-cost technology compared to other technologies such as optical sensing. Thus, the instrumented wearable devices described herein may be used in a wide range of applications that require accurate yet low-cost sensing.

In some examples, a wearable device described herein may include at least one sensor for sensing changes in a patient's heart rate or changes in the water content of a patient's body. Such sensors may be included in a device in addition to, or instead of, the tissue elasticity or size sensors described above. In many cases, the device may be coupled to a wearable, stretchable material; or, in other cases, the device may be capable of being otherwise coupled to the patient's body (e.g., via one or more garments, bands, or adhesive patches).

In further examples, the wearable devices described herein may include or be in communication with a controller module configured to control the delivery of an electrical signal to one of the wearable sensors and/or detect changes in the measurements of selected physiological parameters. The device may also include or be in communication with a processing module configured to determine whether a sensed parameter exceeds a threshold value and/or a communication module configured to deliver an alert signal to a remote computing device capable of alerting a user that a threshold value has been exceeded. In this manner, the devices and systems described herein may monitor changes to a condition (e.g., heart failure) of a patient and alert a user (e.g., the patient or a healthcare professional) that the condition has changed and/or requires medical intervention. In addition to providing benefits pertaining to sensing accuracy and cost, such systems also may improve patient compliance by providing improved ease of use compared, for example, to methods that may require the patient to manually measure and report body weight.

Although the methods and systems for monitoring physiological parameters are generally discussed with regard to cardiovascular disease such as heart failure, the devices, systems, and techniques described herein may be applicable to monitoring other patient conditions and/or symptoms. For example, edema (or swelling) can occur due to a variety of medical reasons other than heart failure. Edema is swelling caused by excess fluid trapped in the body's tissues and is most common in the feet, legs, hands, and face. Edema typically occurs in response to injury or inflammation, but edema can also occur as a result of a number of medical conditions, including heart disease (congestive heart failure), preeclampsia, liver disease, kidney disease, lymphedema, critical illnesses, and in response to medications.

The wearable devices and systems, e.g., a magnetic size sensor described herein, has biomedical applications beyond monitoring of heart failure status. It can, for example, be used for detection of edema, which in turn can be indicative of progress in disease status of a number of medical conditions. In other examples, magnetic size sensors, tissue-elasticity sensors, and other devices described herein may be used to monitor physiological changes due to growth, physical activity or lack thereof, or other conditions.

FIG. 1A is a conceptual illustration of example instrumented sock 8 (e.g., a wearable device that includes multiple wearable sensors), which includes stretchable material 6, leg-size sensor 10, tissue-elasticity sensor 60, water-content sensor 190, and controller module 15. The aforementioned components can be electrically connected via flexible conductive threads 18 (referenced generally) (e.g., LIBERATOR® 40 Silver available from Syscom Advanced Materials of Columbus, Ohio). As illustrated, the threads 18 can be sewn into the instrumented sock 8 in a generally zig-zag pattern to accommodate stretching of the sock 8 as it is taken on and off of the patient. As generally depicted in FIG. 1C, the instrumented sock 8 can also optionally include a zipper 19 to accommodate people who have a large leg size and to enable easier wearing of the sock. Leg-size sensor 10, which further includes inductor 11 and magnetic sensors 12A and 12B, may be coupled to the instrumented sock 8 just above the position of the ankle when the instrumented sock 8 is worn by a patient. Although primarily described as having two magnetic sensors 12A and 12B, any number of magnetic sensors 12A, 12B may be included in leg-size sensor 10. The positions of leg-size sensor 10, tissue-elasticity sensor 60, water-content sensor 190, and controller module 15 are representative and may be different in other examples. In other examples, the instrumented sock 8 may include additional or alternative sensors such as a heart rate sensor to detect heart rate variability or other sensor to detect parameters indicative of heart failure or another condition. In some examples, the instrumented sock 8 may include a posture sensor (e.g., one or more accelerometers or gyroscopes) to determine the relative position of the leg wearing the instrumented sock 8. Since measured parameters on a leg that is horizontal may be different than parameters measured for a leg vertical when the patient is standing or sitting, position information may be used to calibrate the output of sensors on the leg. In other examples, the instrumented sock 8 may include a force sensor on the bottom of the instrumented sock 8 to detect when the patient's foot is on the ground with contact pressure (i.e., the leg is vertical) or the patient foot does not provide pressure (i.e., the leg is elevated). In further embodiments, as generally depicted in FIG. 1D, the instrumented sock 8 can include an elastic band 20 located at the internal side of the instrument sock 8, underneath the inductor 11 and the two magnetic field sensors 12A, 12B.

Figure 1B:
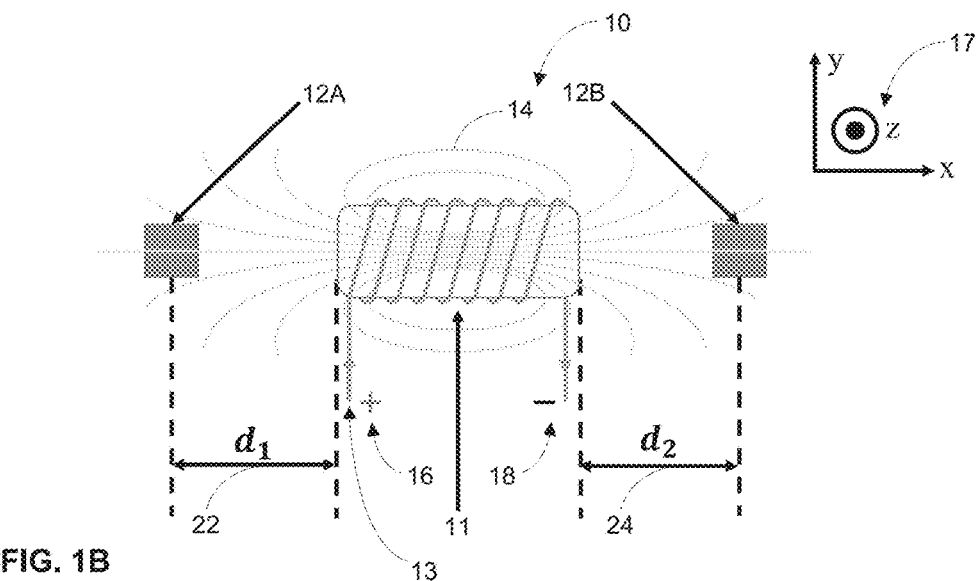
FIG. 1B is a conceptual illustration of an example leg-size sensor, which includes two magnetic field sensors and an inductor to which a voltage has been applied.
Figure 1C:
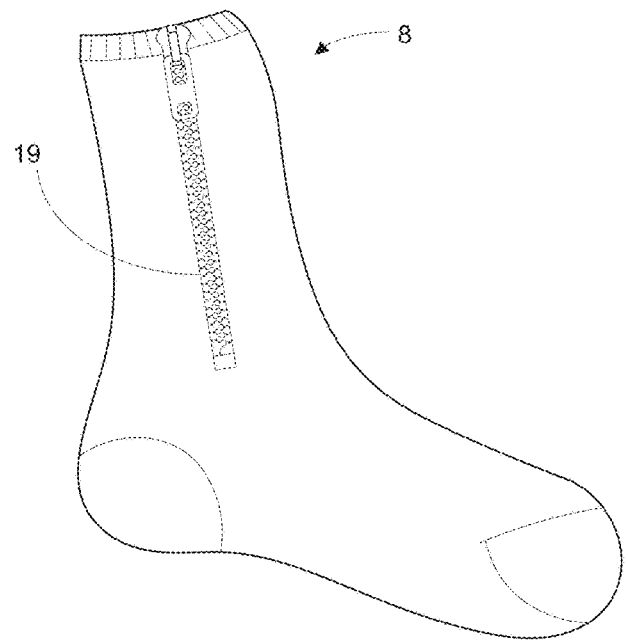
FIG. 1C is a partial, conceptual rear illustration of the instrumented sock of FIG. 1A.
Figure 1D:
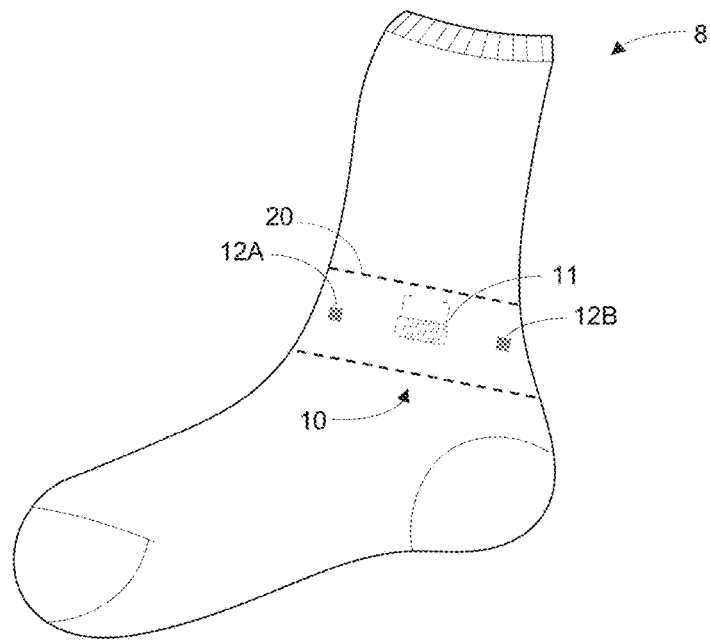
FIG. 1D is a partial, conceptual illustration of the instrumented sock of FIG. 1A.

FIG. 1B is a conceptual illustration of example leg-size sensor 10, which includes two magnetic field sensors 12A and 12B and inductor 11 to which a voltage has been applied at positive terminal 16 via conductive wire 13 (e.g., conductive thread 18 in FIG. 1A). When a voltage is applied to the inductor 11, the inductor 11 acts as a bar magnet and generates magnetic field 14. When a patient's leg swells, distances $d_1$ and $d_2$ between the inductor 11 and the magnetic field sensors 12A, 12B may become larger; consequently, the magnetic field 14 generated by the inductor 11 and sensed by the magnetic field sensors 12A, 12B may become smaller. In other words, if there is a monotonic functional relationship between the sensed intensity of the magnetic field 14 and distances $d_1$ and $d_2$, then a distance measurement pertaining to the circumference of a patient's leg or other body part may be obtained from magnetic field measurement.

As illustrated by graph 17 of FIG. 1B, the magnetic field sensors 12A, 12B may be capable of providing sensor readouts from three axes (x-axis, y-axis, and z-axis). This feature may contribute to the robustness of the measurement provided by the leg-size sensor 10, should the magnetic field sensors 12A, 12B happen to become misaligned from a centerline of the inductor 11. In the case of a misalignment of the magnetic field sensors 12A, 12B with the inductor 11, the influence from a misaligned axis may be eliminated by using the readouts from the other two axes.

The inductor 11 (a.k.a. an electromagnet) may be used in example leg-size sensors described herein instead of a permanent magnet. The use of the inductor 11 may be beneficial because magnetic field sources other than the magnetic field 14 may be present in a patient's environment. For example, both the earth's magnetic field and ferrite-based objects in proximity to a patient may exert an influence on the leg size sensor 10 of FIG. 1B. Thus, in addition to the electromagnetism of the inductor 11, the magnetic field 14 exerted on the magnetic field sensors 12A, 12B may actually be combined with magnetic fields from other sources, thereby resulting in an inaccurate leg size measurement. To account for such magnetic field influences from a patient's environment, a time varying voltage may be applied at a positive terminal 16 of the inductor 11, as described next with regard to FIGS. 2A and 2B.

Figure 2A:
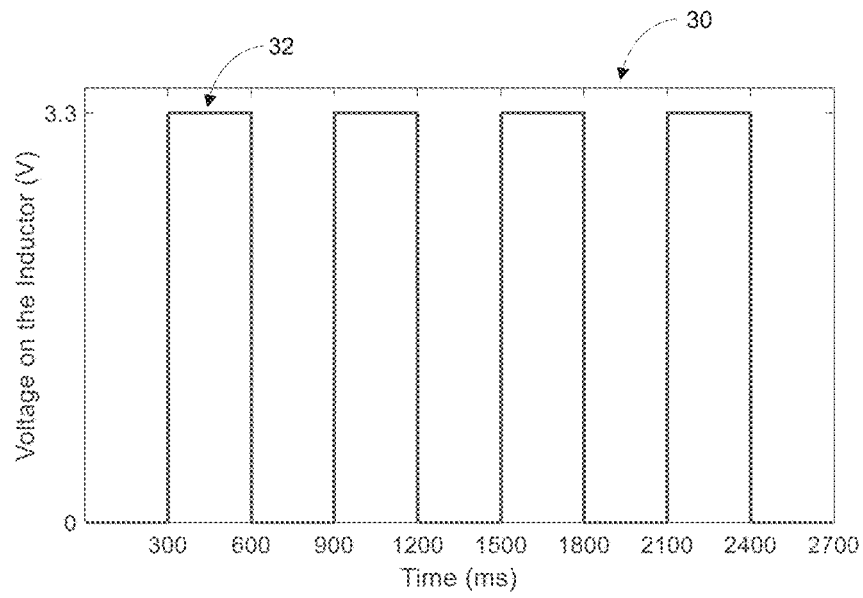
FIG. 2A is a graph illustrating an alternating voltage applied on an inductor.

FIG. 2A is a graph illustrating an application of a periodically varying voltage to one example inductor 11. Using the leg-size sensor 10 of FIG. 1B as an example, an AC voltage, varying between 0 Volts and 3.3 Volts every 300 milliseconds, may be applied to the positive terminal 16 of the inductor 11. Other voltage changes may be used in different examples. As shown by graph 30, the intermittent application of 3.3 Volts at the terminal 16 of the inductor 11 can be visualized by roughly square-shaped peak 32 in FIG. 2A.

Figure 2B:
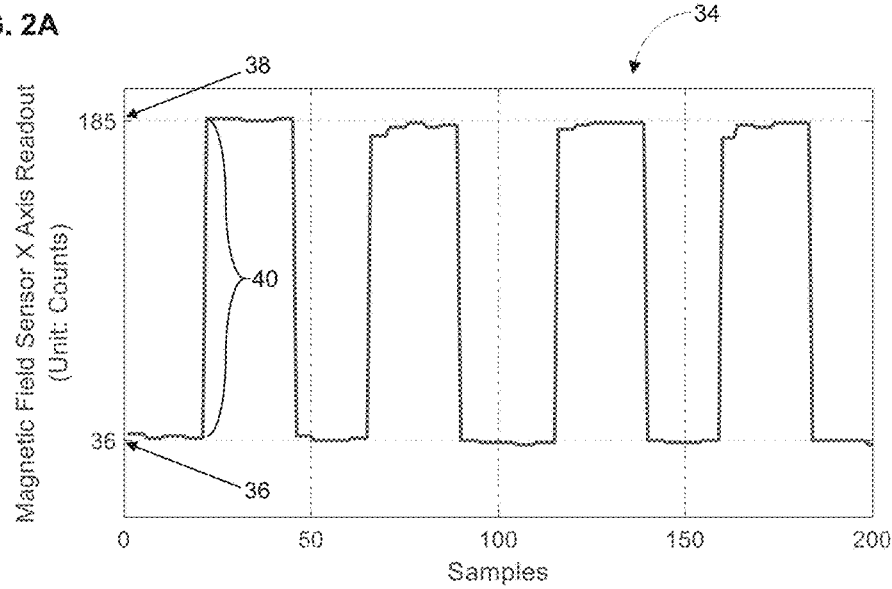
FIG. 2B is a graph illustrating the readout of a magnetic field sensor due to a voltage applied on an inductor, combined with the magnetic field from both the inductor and the environment.

FIG. 2B is a graph illustrating a readout of the example magnetic field sensor 12A in response to the application of the varying AC voltage of FIG. 2A on the example inductor 11. As shown by graph 34, the application of a varying AC voltage on example inductor 11 may result in a response that accounts for the combination of a magnetic field from both the inductor 11 and the environment (reading 38), whereas reading 36 reflects the magnetic field from the environment only. Hence peak-to-peak range 40 of graph 34 reflects the magnetic field from inductor 11 only. Thus, the magnetic influence from a patient's environment may be eliminated, and peak-to-peak range 40 may function as a reliable indicator of a patient's leg size. It should be noted that changes in environmental magnetic fields, or other slowly-varying magnetic fields, will only cause a change in bias of the magnetic field sensed by magnetic field sensors 12A, 12B, and will not change peak-to-peak range 40 in response to the applied AC signal. The application of peak-to-peak range 40 further applies to selection of the number of magnetic field sensors 12A, 12B, as described next with reference to FIGS. 1A and 1B.

With further regard to FIG. 2B, some examples described herein include at least two magnetic field sensors 12A, 12B, as shown in FIGS. 1A and 1B. Such a configuration may help compensate for an unequal distribution of a stretchable material 6 of device 8 about the circumference of a patient's leg. Prior to an increase in leg size, two magnetic field sensors 12A, 12B may be situated equidistant from the inductor 11 such that $d_1$ and $d_2$ of FIG. 1B may be equal to one another. When a patient's leg size increases, such as may occur in response to an accumulation of fluid in the lower extremities, stretchable material 6 of device 8 may stretch, thereby increasing the distance between the magnetic field sensors 12A, 12B and the inductor 11. However, since friction may be present between example device 8 and the patient's skin, the stretch of stretchable material 6 may be unevenly distributed around the circumference of a patient's leg. Thus, after the patient's leg swells, $d_1$ and $d_2$ generally may not remain equal, thereby indicating that the readout of the magnetic field sensors 12A, 12B may be related to the stretch of stretchable material 6 located between the magnetic field sensors 12A, 12B and the inductor 11. Therefore, configurations including at least two magnetic field sensors 12A, 12B may permit the generation of multiple peak-to-peak ranges 40, which in turn may allow a subsequent averaging of multiple peak-to-peak ranges 40 as an indicator of leg size.

Figure 3:
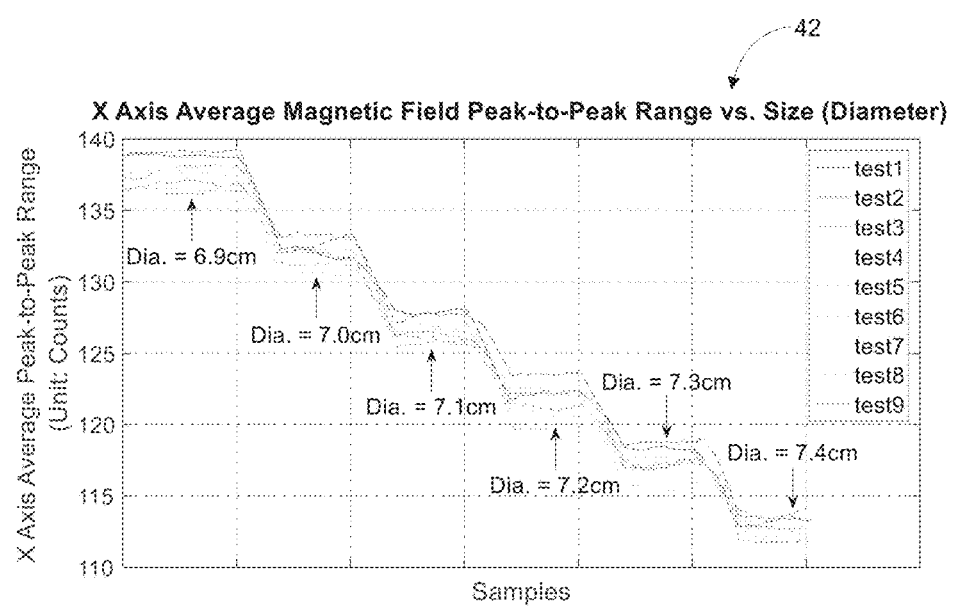
FIG. 3 is a graph illustrating the average magnetic field peak-to-peak range produced by a size sensor placed on different layers of a test object having layers of varying diameters.

FIG. 3 is a graph illustrating the average magnetic field peak-to-peak range 40 of FIG. 2B, as experienced by an example leg-size sensor placed on a 21-layer test conicle having a linearly varying diameter in 1 mm increments. The diameters of the test conicle ranged from 6 cm to 8 cm, thereby representing the diameter range of typical human legs. To carry out the test, the size sensor was placed on the 6.9 cm-diameter layer and then an average peak-to-peak range from the x-axis readouts for the 6.9 cm-diameter layer was obtained. This test was repeated for each layer having diameters between 7.0 cm and 7.4 cm. After multiple repetitions of the test for each tested diameter, a comparison of all the test results was generated in chart 42. As shown in chart 42, the influence of an environmental magnetic field on body-part size sensing may be eliminated by averaging peak-to-peak ranges for each diameter size tested. Further as shown in chart 42, the accuracy of the example leg-size sensor may be better than 1 mm. Discussion and examples for modeling the size of a leg using leg-size sensor 10 are provided in Appendix A attached herein.

Figure 4A:
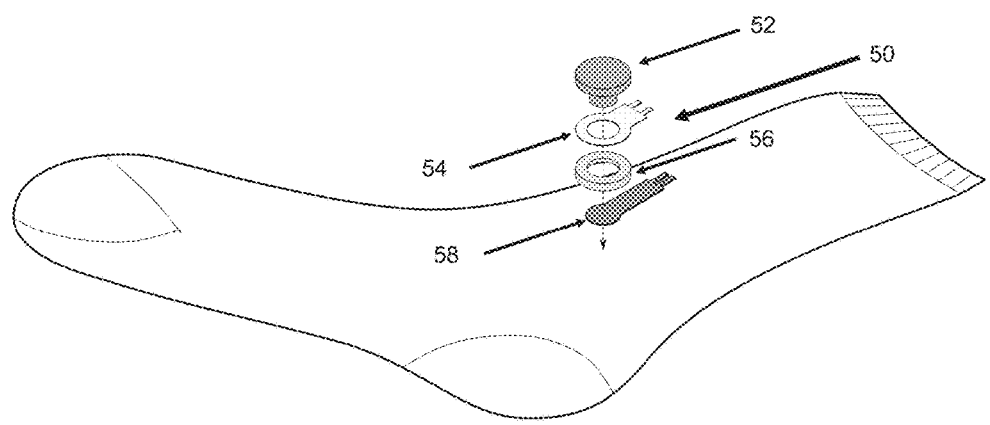
FIG. 4A is an exploded view of the components of an example elasticity sensor, including a first force sensor, a plastic ring, a second force sensor, and a plastic button.

FIG. 4A is an exploded view of the components of an example elasticity sensor 50 ("tissue-elasticity sensor 50"), including a first force sensor 58, a plastic ring 56, a second force sensor 54, and a plastic button 52. Tissue elasticity can be sensed with indentation-type tissue stiffness test, though this method requires either controlled displacement or controlled force. Additionally, a test utilizing the shift in resonant frequency of a vibrating transducer in contact with a soft material can be used, but presents miniaturization problems due to the need for an actuator. Micro-electro-mechanical systems (MEMS) devices, based on the concept of using two flexible sensing elements with considerably different stiffness values, may be suitable for miniaturization, but may display large variance in readouts due to the use of soft materials and imperfections in its complicated fabrication process. The example tissue-elasticity sensors described herein, however, are easily miniaturized, simple to use and manufacture, and yet may provide relatively high reliability compared to other examples.

Figure 4B:
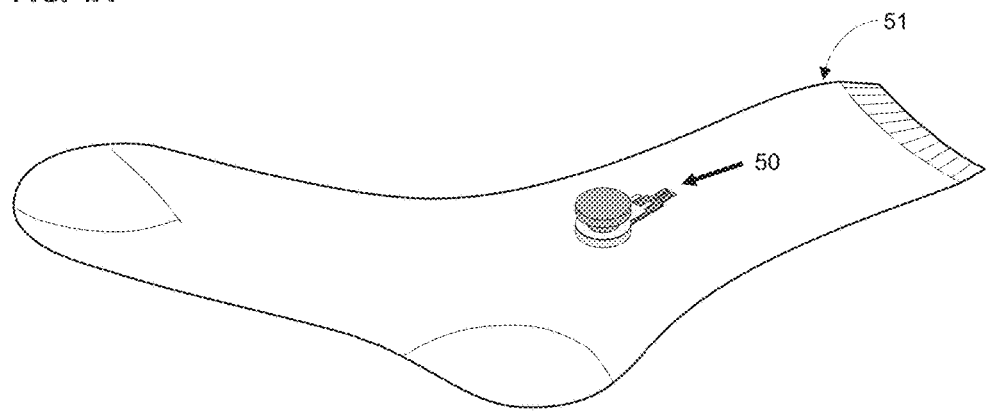
FIG. 4B is a perspective view of an example assembled elasticity sensor, having the components of the example sensor of FIG. 4A.

FIG. 4B is a perspective view of the assembled tissue-elasticity sensor 50 coupled to an example wearable device 51. The tissue-elasticity sensor 50 provides forces to two different areas of the tissue in response to pressure applied to the plastic button 52. Since one area is indented prior to the other area of the tissue, the rate of change in forces compared between the two force sensors of sensor 50 can provide an indication of the tissue elasticity when used. In some examples, an automated pressure application apparatus may be used to periodically execute the elasticity test without patient or user intervention.

Figure 5A:
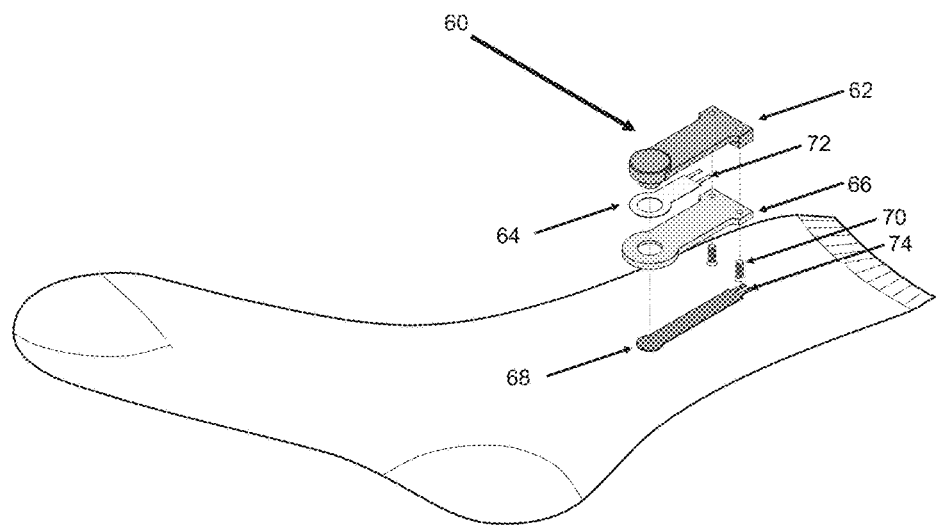
FIG. 5A is an exploded view of the components of another example elasticity sensor, including a first force sensor, a plastic holder, a second force sensor, a plastic lever having a rounded top portion, and several fasteners.

FIG. 5A is an exploded view of the components of another example tissue-elasticity sensor 60 ("tissue-elasticity sensor 60"), including a first force sensor 68 having electrodes 74, a plastic holder 66, a second force sensor 64 having electrodes 72, a plastic lever 62, and fastening screws 70. The tissue-elasticity sensor 60 may have similar components to the tissue-elasticity sensor 50; however, the plastic button 52 and the plastic ring 56 of the tissue-elasticity sensor 50 may be modified to the plastic lever 62 and the plastic holder 66 of the tissue-elasticity sensor 60, so as to provide well-aligned, repeatable motion with little variance. Therefore, while numerous embodiments are possible, the tissue-elasticity sensor 60 primarily is described herein.

Figure 5B:
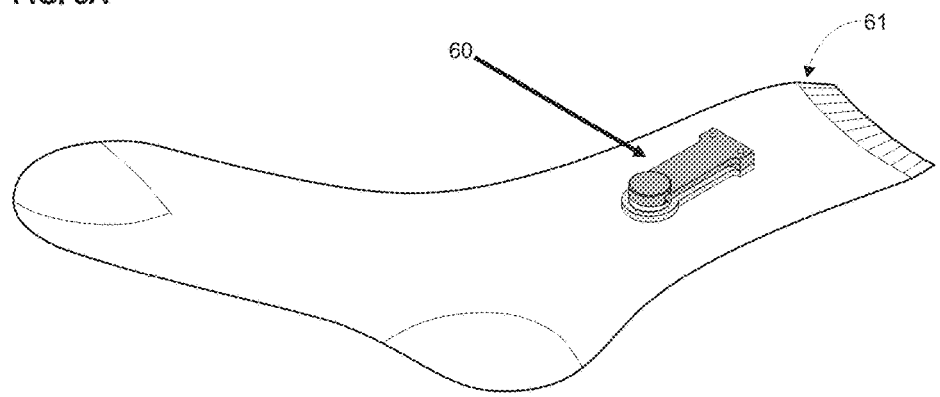
FIG. 5B is a perspective view of an example assembled elasticity sensor, having the components of the example sensor of FIG. 5A.

FIG. 5B is a perspective view of the assembled tissue-elasticity sensor 60 coupled to an example wearable device 61. Similar to the sensor 50 of FIG. 4B, the differences in forces from the two force sensors of the sensor 60 can be plotted to determine the elasticity, or stiffness, of the tested skin or tissue sample.

Figure 6:
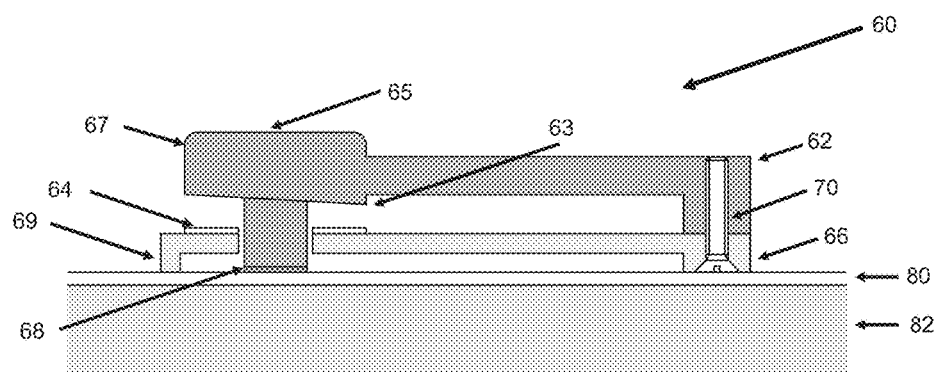
FIG. 6 is a side view of the example elasticity sensor of FIG. 5B coupled to the stretchable material of a sock and worn on the foot of a user.

FIG. 6 is a side view of the tissue-elasticity sensor 60 of FIG. 5B coupled to an example wearable device 80 and worn adjacent to leg tissue 82 of a user. During use of the tissue-elasticity sensor 60, a patient may simply use a thumb to press the button portion 65 of the plastic lever 62. As described with regard to FIGS. 7A-7C, there are three key moments that occur during the motion of the plastic lever 62.

The tissue-elasticity sensor 60 may provide some advantages over the tissue-elasticity sensor 50. For example, instead of a pure button, the top part now is made into a lever with a button at one end and is fixed to the plastic holder at the other end using two screws. At the button end of the plastic lever, a protruding boss 67 with rounded top is made for letting the patient or doctor easily press the button. Due to the lever structure, the path taken by the button is no longer a line, but a small curve in the sensor 60 about a pivot located at the position of the screws with large radius of curvature, therefore an inclined surface 63 is designed at the bottom side of the lever to ensure that the button will touch the second force sensor 64 firmly and uniformly. The advantage of using a lever in sensor 60 instead of using just a button hanging freely in sensor 50 is that this makes the button start from the same position and go through an almost identical path every time when being pressed, which will help to improve the reliability of the disclosed elasticity sensing. The beam/lever acts as a spring that restores the top button to its original position when the force from the user is released. Also, the lever of sensor 60 provides consistent aligned movement of the top button to minimize tilted non-uniform misaligned movement.

Figures 7A, 7B, 7C:
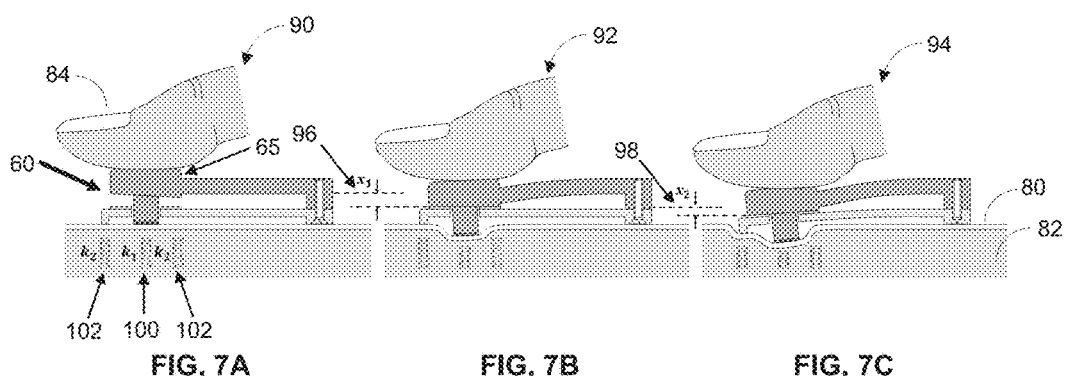
FIGS. 7A-7C are side views of different moments caused by a user's thumb pushing the plastic lever of the example sensor of FIG. 5B.

FIG. 7A is a side view of moment I 90, in which user's thumb 84 has begun to push the plastic button 65 of the plastic lever 62 of the tissue-elasticity sensor 60. One may assume that the leg tissue 82 underlying the first force sensor 68 behaves like spring 100 having elasticity $k_1$, and that the leg tissue 82 underlying both ring portion 69 of the plastic holder 66 and the second force sensor 64 behaves like springs 102 having elasticity $k_2$. At moment I 90, spring 100 and springs 102 are at their undeformed lengths. To determine the value $k_1$, since $$k_1 = \frac{F_1}{x_1} \quad (1)$$

the displacement $x_1$ can be a known constant during the measurement process, then a measure of the corresponding force $F_1$ can be used as an indicator of stiffness or elasticity.

FIG. 7B is a side view of moment II 92, in which the plastic lever 62 of the tissue-elasticity sensor 60 has begun to move in response to being pushed by the user's thumb 84. Between moment I 90 and moment II 92, the plastic holder 66 does not move, and only the button portion 65 of the plastic lever 62 is pushed by the user's thumb 84. Moment II 92 can be characterized as the moment the plastic button 65 of the plastic lever 62 just touches the ring portion 69 of the plastic holder 66, at which time the plastic button 65 has just been pushed by a distance of $x_1$. The distance $x_1$ by which the button portion 65 has been pushed can be reflected in the deflection of leg tissue 82 underlying the first force sensor 68, as illustrated by the compression shown at the spring 100. Since $x_1$ is a value determined only by the structure of the plastic button 65 and the ring portion 69 of the plastic holder 66, $x_1$ is a constant. The force readout from the first force sensor 68 thus may be calculated at moment II 92, which may function as an indicator of tissue elasticity and be accomplished by setting:

$$F_{Target} = k_1 x_1 \quad (2)$$

in which the assumption may be made that the curvilinear motion traced by button 65 can be approximated as a line.

FIG. 7C is a side view of moment III 94, in which both the plastic lever 62 and the plastic holder 66 of the tissue-elasticity sensor 60 have been pushed by a distance of $x_2$. Between moment II 92 and moment III 94, the plastic button 65 and the ring portion 69 of the plastic holder 66 move together. At moment III 94, the plastic button 65 and the ring portion 69 of the plastic holder 66 have just been pushed by another distance of $x_2$. The distance $x_2$ by which the plastic button 65 and ring portion 69 of the plastic holder 66 has been pushed can be reflected in the deflection of leg tissue 82 underlying both the ring portion 69 of the plastic holder 66 and the second force sensor 64, as illustrated by the compression shown at springs 102. The readouts from the first force sensor 68 and second force sensor 64 may be denoted $F_{S1}$ and $F_{S2}$ respectively; then, $F_{S1}$ and $F_{S2}$ can be expressed as:

$$F_{S1} = k_1(x_1 + x_2) \quad (3)$$

$$F_{S2} = k_2 x_2 \quad (4)$$

Using Equation (2), Equation (3) can be rewritten as:

$$F_{S1} = F_{Target} + k_1 x_2 \quad (5)$$

Therefore, a relationship may be established between $F_{S1}$ and $F_{S2}$ as follows:

$$F_{S1} = \frac{k_1}{k_2} F_{S2} + F_{Target} \quad (6)$$

Thus, a line may be fit between readouts from the two force sensors $F_{S1}$ and $F_{S2}$. The intercept of this fitted line, $F_{Target}$, may be used as an indicator of tissue elasticity which is further described in FIGS. 8A-8C.

Figure 8A:
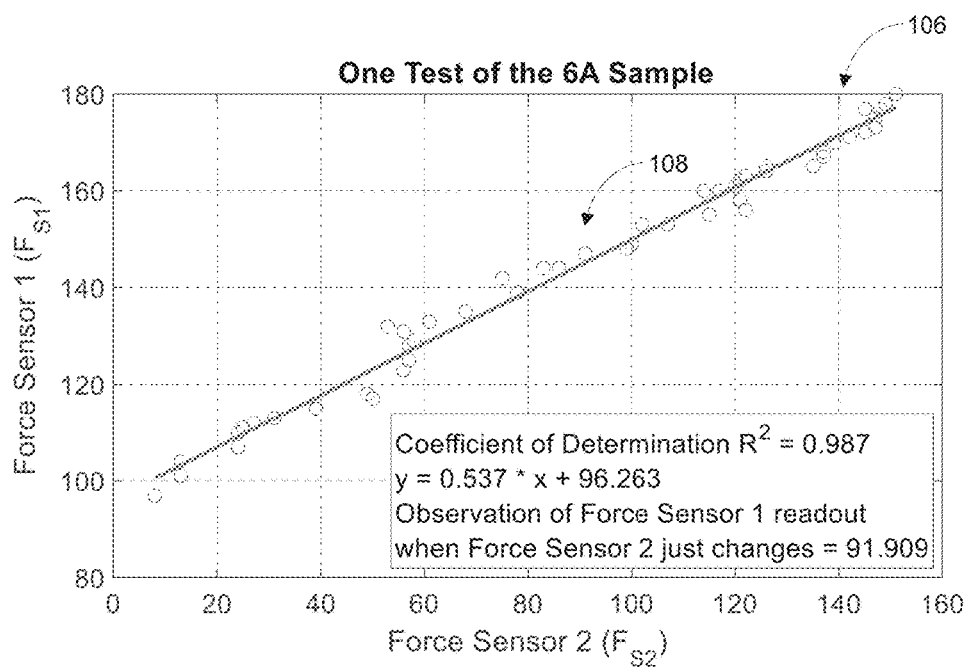
FIG. 8A is a graph illustrating the results of one test of an example tissue-elasticity sensor on a sample material.

FIGS. 8A-8C collectively are graphical illustrations of the comparative results of a series of tests of the tissue-elasticity sensor 60 upon five sample materials having elasticity values from 6 A to 10 A. On each sample material, ten tests were conducted using the tissue-elasticity sensor 60. FIG. 8A is a graphical illustration of the results of one test of the tissue-elasticity sensor 60 on the 6 A sample. The units on the x-axis and y-axis are Counts, in linear proportion to Newtons. As shown in graph 106, the force readout from $F_{S1}$ (first force sensor 68) is shown vs. the force readout from $F_{S2}$ (second force sensor 64) form line 108, thereby justifying the assumptions made during the modeling process described herein. Furthermore, line 108 further verifies the feasibility of the tissue-elasticity sensors described herein. In other words, elasticity of the tissue can be determined based on the intercept of the line formed by the forces plotted from each force sensor of the sensor 60.

FIG. 8B is a graphical illustration of comparison of the ten tests conducted on each of the five sample materials having elasticity values from 6 A to 10 A. The y-axis of chart 110 indicates a force (Unit: Counts, in linear proportion to Newtons), and the x-axis of chart 110 indicates the elasticity of the test samples as indicated by each sample's Shore number on the Shore scale for soft material stiffness (i.e., increasing numbers indicate increasingly stiff materials on the right of the chart). As shown in chart 110, data points 112 for the ten tests conducted on each sample material are grouped closely together, indicating high accuracy of the readouts of the tissue-elasticity sensor 60.

FIG. 8C is an error bar graph illustrating a monotonic trend of readouts from the tissue-elasticity sensor 60 for the five sample materials tested in chart 110 of FIG. 8B. The y- and x-axes of chart 120 indicate the same variables as those indicated in chart 110 of FIG. 8B. As shown by line 122 of chart 120, the monotonic trend of increased intercept with decreased elasticity (increased hardness) is consistent among readouts of the tissue-elasticity sensor 60 for each sample material.

In some examples, devices and systems described herein may include sensors for the detection of changes in the water content of a patient's body, as water content provides another physiological parameter that may change when an ADHF is imminent, or as the heart failure status of the patient changes over time. In some examples, the water content of a patient's body may be measured using bioelectrical capacitance or dielectric constant measurement. Such a method for measuring water content may be preferable over other examples for numerous reasons. For instance, imperfect contact (inadequate contact force) between electrodes of an example device and a patient's skin may cause significant contact resistance and inaccurately bias the reading of the bioelectrical resistance of the patient's body. Alternatively, imperfect contact between the electrodes of an example device and a patient's skin may have very minor influence on measured capacitance of the tissue. A gap of tens of microns or even hundreds of microns may be insignificant compared to the several millimeters of tissue thickness that provide the capacitance being measured. Thus, measurement of bioelectrical capacitance instead of bioelectrical resistance may be less susceptible to bias due to imperfect contact.

Furthermore, while bioelectrical impedance analysis may be used to estimate the total water content in the body, it is not a localized technique. Bioelectrical impedance measures whole body water content, which renders such methods less useful for determining localized water content near the ankles or in the lower leg that may be indicative of an impending ADHF. Bioelectrical capacitance measurement, however, as employed by example water-content sensors herein, may be a localized measurement technique in which the skin and tissue just below the skin create fringe capacitance on two electrodes placed in contact with the skin. The fringe capacitance created on such electrodes therefore may be highly influenced by the local tissue close to the electrodes, whereas the rest of the body may not have influence on the fringe capacitance.

Figure 9:
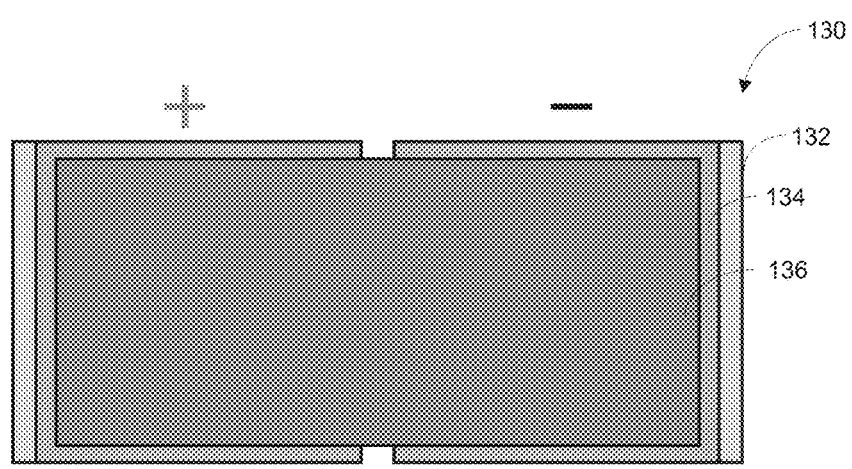
FIG. 9 is a top view of a thin-film, flexible capacitance-measuring device for water-content sensing and for wearable applications.

FIG. 9 is a top view of a thin-film, flexible capacitance-measuring device 130 for water-content sensing and for wearable applications. The device 130 may consist of thin, outer metallic film 136, which may be fabricated from silver ink, or from another conductive material. The device 130 may further consist of insulation film 134 and one or more planar thin film electrodes 132 placed adjacent to each other on a wearable device to which the device 130 may be coupled. Outer metallic film 136 may serve as a Faraday cage, thereby preventing the influence of fringe capacitance from outside a patient's body on the capacitance measured between the electrodes 132. The capacitance between the electrodes 132 thus may be influenced only by the fringe capacitance from patient's own body. The entire device 130 may be flexible, so as to allow for fabrication on the inner surface of a wearable device to which the device 130 may be coupled.

Figure 10:
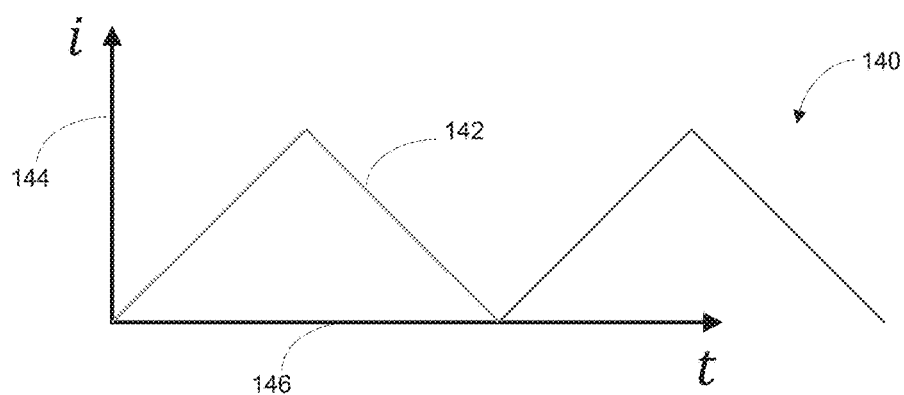
FIG. 10 is a graph illustrating an example method for obtaining a capacitance measurement.

FIG. 10 is a graph illustrating an example method for obtaining a capacitance measurement, in which current 144 supplied to a capacitor of a water-content sensor is varied by a microcontroller as a function of time 146 (e.g., ramped up and ramped back down over time). As shown in chart 140, current 144 supplied by a microcontroller may vary periodically. Other shapes of current variation (e.g., sinusoidal in contrast to the triangular shape illustrated in FIG. 10) may be used in different examples. The resulting measured capacitance may be indicative of water content in the measured tissue.

Figure 11:
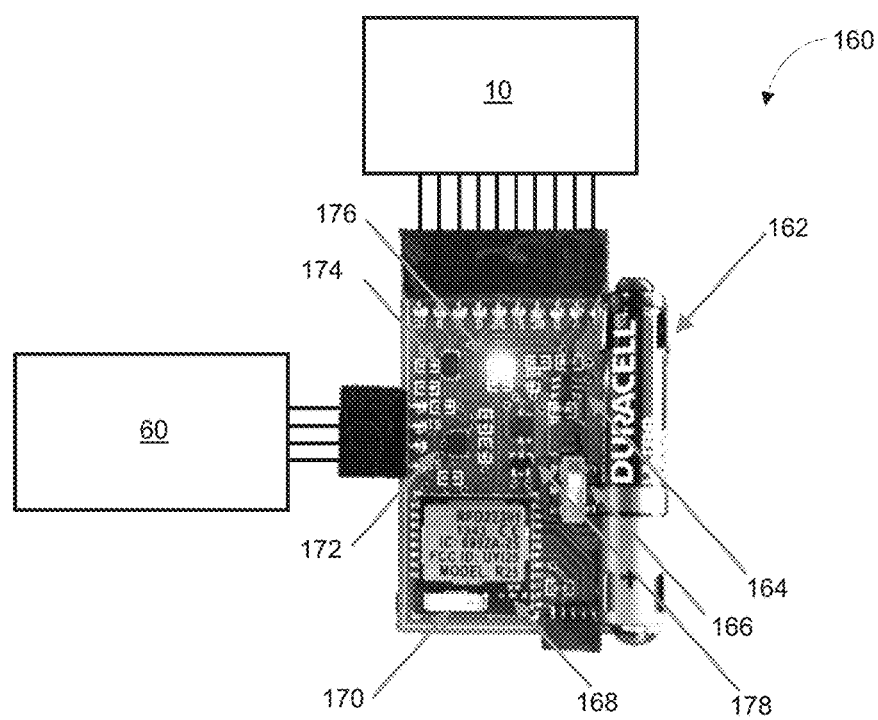
FIG. 11 is a conceptual view of a wireless-enabled system including a microcontroller.

FIG. 11 is a conceptual view of the wireless-enabled system 160 including a leg-size sensor 10, tissue-elasticity sensor 60, battery 162, voltage regulator circuit 164, switch 166, microcontroller 168, antenna for wireless communication 170, operational amplifier 172, multiplexer 174, MOSFET and diode 178, and status LED 176. In some examples, the microcontroller 168 is configured to control delivery of an electrical signal to an electromagnet (e.g., the inductor 11 of FIG. 1A) and receive, from each of one or more magnetic field sensors (e.g., the magnetic field sensors 12A, 12B of FIG. 1A), a respective signal indicative of a magnetic field. The microcontroller 168 may be further configured to determine a heart failure status of a patient based on a size measurement of a leg or other body part detected using the signal(s) received from magnetic field sensors and/or determine an elasticity detected from a tissue portion of a patient using signals received from a tissue-elasticity sensor (e.g., the tissue-elasticity sensor 60 of FIG. 5B). This wireless-enabled system 160 may be an example of the controller module 15 of the instrumented sock 8 in FIG. 1A. In some examples, the system 160 may include or be in communication with a sensor for detecting water content of the patient using signals received from a water-content sensor (e.g., the water-content sensor 190 of FIG. 13A. The system 160 may also include or be in communication with a heart-rate sensor for detecting heart rate variability.

Communication of a heart-failure status of a patient may then be transmitted from the microcontroller 168 to an antenna for wireless communication 170, which in turn may transmit a communication pertaining to the heart-failure status to a remote computing device (e.g., a mobile computing device operated by the patient or another user or a networked server configured to present application to a healthcare professional). In this manner, information from the system 160 may be sent to another device that provides monitoring of the patient or can prompt the patient or a healthcare provider to seek medical attention. The user, or a computing device, may also be able to review changes to physiological parameters that occur over time to determine any trends that may be indicative of heart failure. Voltage regulator circuit 164 and battery 162 may ensure a stable supply of power to the wireless-enabled system 160. Multiplexer 174 permits multiple devices to be connected with the microcontroller 168; for example, the two magnetic field sensors 12A and 12B, who have the same $I^2C$ addresses, in FIGS. 1A and 1B. Operational amplifier 172 converts the forces exerted on the force sensors 64 and 68 in FIG. 5A to electrical signals. MOSFET and diode 178 permit generating a reliable alternating voltage to supply to the inductor 11 in FIGS. 1A and 1B. Status LED 176 may provide a visual indication to a user of a condition or an alert; for example, an indication that a measurement has exceeded a threshold value, or that the wireless-enabled system 160 is operating normally.

The wireless-enabled system 160 provides one example of a complete system described herein for the detection of changes in physiological parameters related to an imminent adverse health event, such as an ADHF, and the communication of the detected changes to a user or to another device. In various embodiments, the wireless-enabled system 160 may include other sensors, such as water-content sensors or heart-rate sensors, in addition to or instead of the leg-size sensor 10 and the tissue-elasticity sensor 60. In some examples, the wireless-enabled system 160 may be coupled to a stretchable material such as the material of a sock; in other examples, the wireless-enabled system 160 may be modified for other applications. Example heart-rate sensors may include sensors implementing photoplethysmography (PPG) to monitor how much blood is present and indicate pulses through arteries. A PPG sensor may include an LED and photodetector(s) to detect changes in blood flow. Motion cancellation algorithms may be implemented using an accelerometer or gyroscope in order to ensure that blood motion is detected. Changes to heart rate can be determined as heart rate variability for the patient as another input in determining the heart failure status.

Figure 12A:
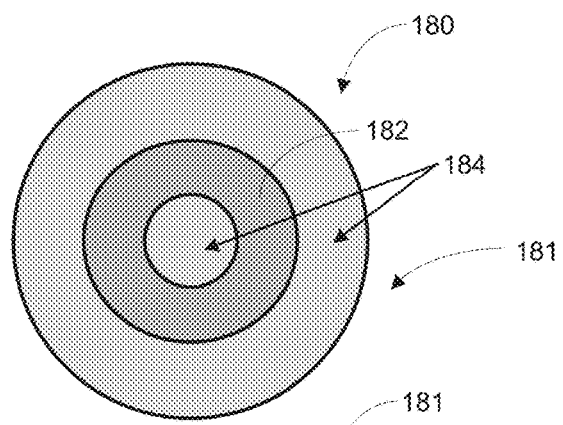
FIG. 12A is a top view of an example water-content sensor including an open-ended coaxial cable.
Figure 12B:
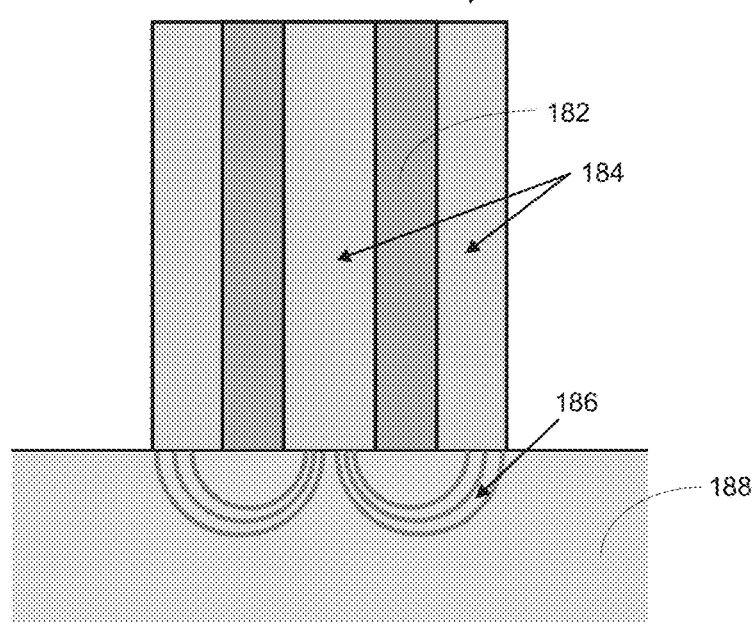
FIG. 12B is a side view of an example water-content sensor including an open-ended coaxial cable.

FIG. 12A is a top view of an example water-content sensor 180 including an open-ended coaxial cable 181, dielectric 182, and electrodes 184. FIG. 12B is a side view of the water-content sensor 180, including an open-ended coaxial cable 181, wherein fringe capacitance 186 may be created across electrodes 184 of the coaxial cable 181 at local tissue 188. Estimation of fringe capacitance 186 thus may allow for estimation of dielectric constant and water-content of the sample tissue. The water-content sensor 180 therefore may provide at least two advantages over bioimpedance measurement, including a relatively lowered sensitivity to any air gap between the sensor 180 and the skin (e.g., local tissue 188). In addition, fringe capacitance 186 may be highly influenced by the local tissue, instead of by whole-body water content.

To measure capacitance, the use of an electrical impedance measurement analyzer is made. Parameter estimation techniques together with appropriately chosen electrical excitation can be utilized. ω has to be chosen in such a way as to have the electrical signal only pass through extracellular fluid, not intracellular (300 MHz).

$$V = \frac{1}{C}\int i \, dt + L\frac{di}{dt} + iR \quad (7)$$

$$\frac{dV}{dt} = \frac{i}{C} + L\frac{d^2i}{dt^2} + R\frac{di}{dt} \quad (8)$$

The system can use a current source. In order to remove the influence of L, keep $$\frac{di}{dt}$$

as constant, so that $$\frac{d^2i}{dt^2} = 0$$

(see FIG. 10 for an example). Use carrier frequency such that only extracellular fluid is involved. Then use a modulation on top of a carrier frequency. Then the system can measure $$\frac{dV}{dt}.$$

Equation (8) can then be used to estimate the parameters R and C.

The dielectric constant can be obtained by measuring the tissue capacitance $C_0$ when there is no fluid accumulation. Then measure tissue capacitance C when there is possible fluid accumulation. The dielectric constant is obtained from:

$$\varepsilon = \frac{C}{C_0} \quad (9)$$

FIG. 13A is a top view of an example water-content sensor 190, including planar adjacent electrodes 194 and dielectric 192. FIG. 13B is a side view of the water-content sensor 190, including planar adjacent electrodes 194, dielectric 192, wherein fringe capacitance 196 may be created across electrodes 194 at local tissue 198. Where a planar-adjacent configuration of electrodes 194 is used, as in the water-content sensor 190, arrays of such planar capacitors or a comb structure of electrodes (e.g., FIG. 14) may be needed for an appropriate nominal capacitance. In the use of some such example water-content sensors, a high frequency (50-300 MHz) voltage may be applied and current subsequently monitored may permit computation of capacitance using estimation algorithms.

FIG. 14 is a conceptual illustration of comb-structure electrodes 200, which may be used in some example water-content sensors described herein. The use of comb-structure electrodes 200 in water-content sensors, such as in the water-content sensor 190, may provide relatively higher sensitivity to fringe-capacitance changes due to changes in water content as compared to conventional electrodes.

Figure 15:
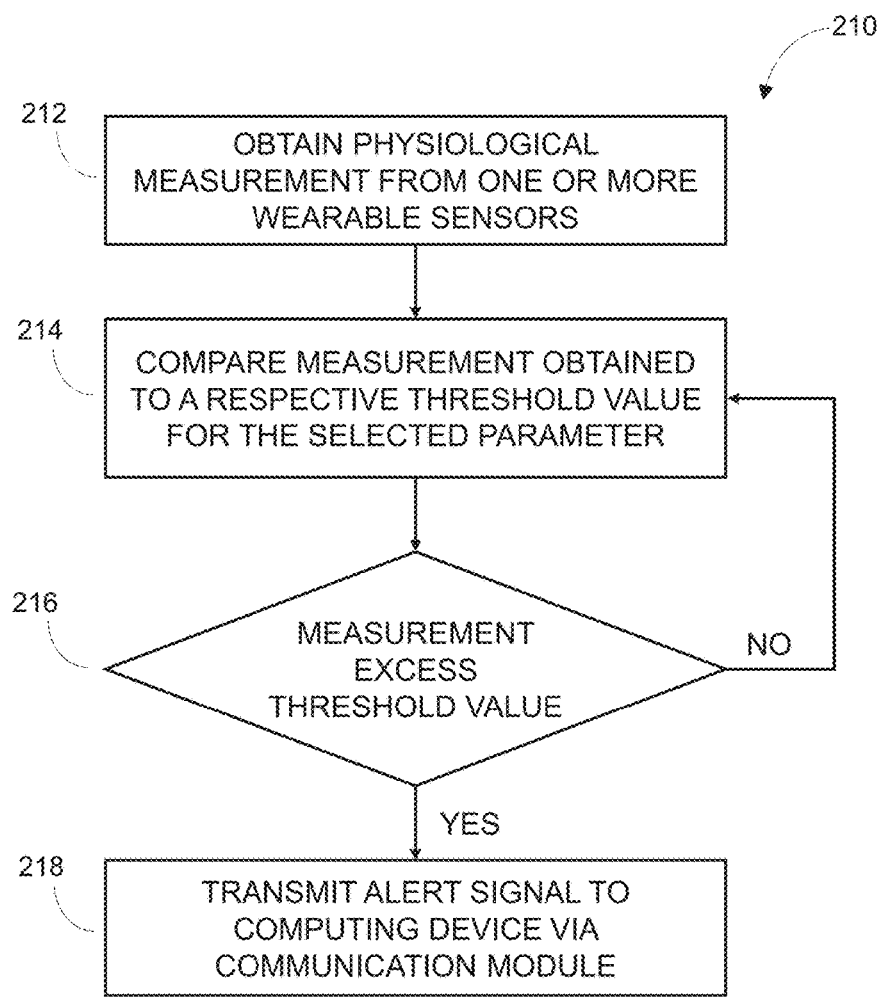
FIG. 15 is a flow diagram illustrating a method for monitoring a heart failure status of a patient.

FIG. 15 is a flow diagram illustrating an example method 210 for monitoring a heart failure status of a patient that may be performed by the instrumented sock 8, in one example. In other examples, the microcontroller 168 of the system 160 in FIG. 11, or a remote computing device in communication with wearable sensors, may perform the method 210. In accordance with the method shown in FIG. 15, the controller module 15 may obtain a physiological measurement for a selected parameter from one or more wearable sensors such as the leg-size sensor 10 and/or the tissue-elasticity sensor 60 (212). The controller module 15 may then compare the measurement obtained from the wearable sensor to a respective threshold value for the selected parameter (214). In some examples, the controller module 15 may determine a heart failure status value based on the one or more measurements and compare the heart failure status value to the respective threshold in order to provide a composite of the measured information.

The controller module 15 may also determine whether the measurement or determined value exceeds the threshold value (216). If the measurement does not exceed the respective threshold value ("NO" branch of the block 216), the controller module 15 may continue to obtain additional measurements (212). If the measurement does exceed the respective threshold value ("YES" branch of the block 216), the controller module 15 may generate and transmit an alert signal to a remote computing device via a communication module (218).

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Figure 16A:
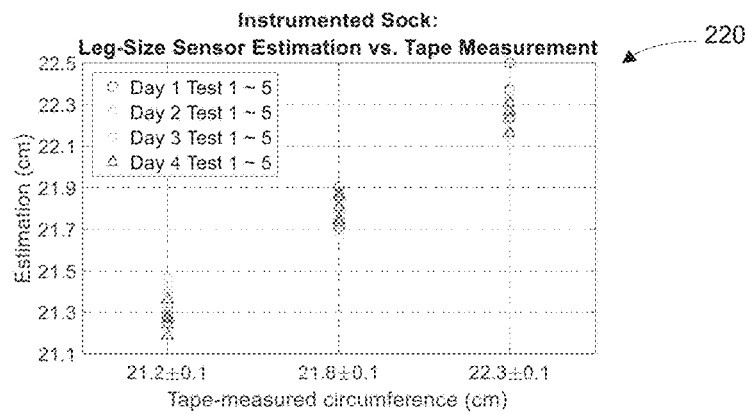
FIG. 16A is a graph illustrating the comparative results of a series of tests of leg-size sensor estimate as compared to a tape measurement.
Figure 16B:
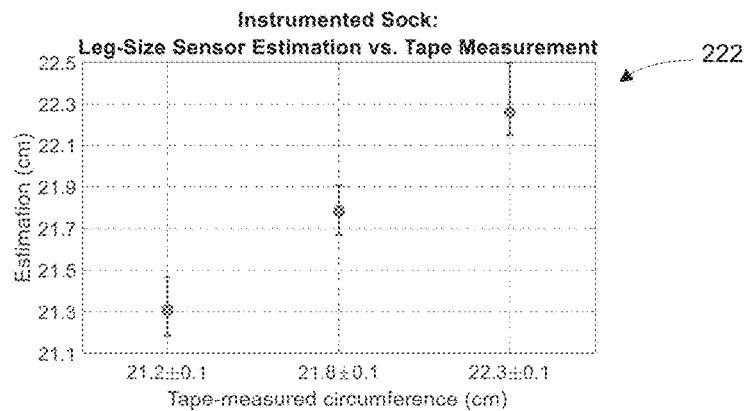
FIG. 16B is a graph illustrating the comparative results of a series of tests of leg-size sensor estimate as compared to a tape measurement.

FIGS. 16A-16B include graphs 220, 222 illustrating the results of testing conducted to compare the measured leg size by the instrumented sock 8 as compared to a tape-measured leg size. To simulate real-world applications, the instrumented sock 8 was put on and taken off a patient's foot, including a portion of the respective leg, 20 times. The patient's "leg size" was artificially enlarged by having the patient wear one or two additional regular socks underneath the instrumented sock (the addition of one regular sock changed the leg radius by 0.8 mm). The change in leg size was measured by the instrumented sock 8 and recorded. The test results indicate that the instrumented sock 8 can sense absolute leg size with no drift. The accuracy was found to be better than 0.8 mm in radius, after repeated human testing.

Figure 17:
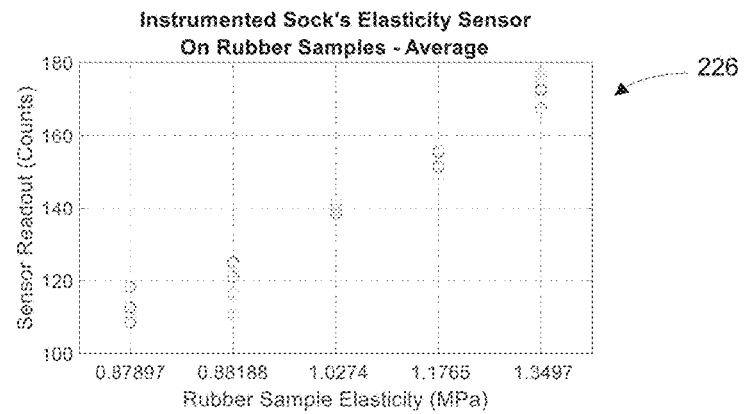
FIG. 17 is a graph illustrating the comparative results of a series of tests of instrumented sock's elasticity sensor on rubber samples.

FIG. 17 includes a graph 226 that illustrates the results of testing conducted to determine the elasticity of rubber samples. The tissue-elasticity sensor 60 of instrumented sock 8 was tested by measuring the elasticity of rubber samples with different known elasticities varying by 0.15 MPa. For each rubber sample, tests were repeated five times. As FIG. 17 illustrates, the accuracy of the elasticity sensor is better than 0.15 MPa.

Figure 18A:
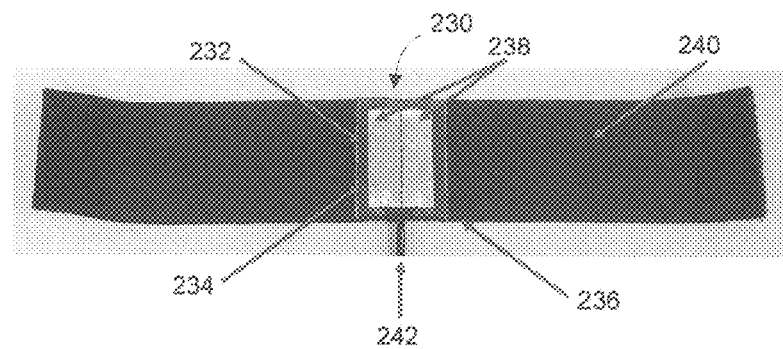
FIG. 18A is a photograph of a water-content sensor.
Figure 18B:
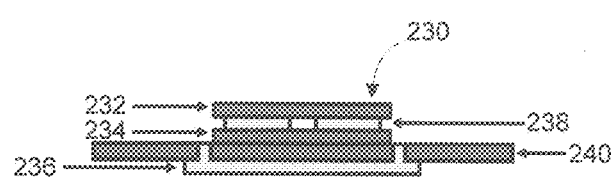
FIG. 18B is an illustration of the water-content sensor of FIG. 18A.

FIGS. 18A-18B illustrate one example of a tissue water-content sensor 230, similar to the tissue water-content sensor 190, secured to an elastic band 240. The tissue water-content sensor 230 having a coplanar capacitor structure, which is composed of two electrodes 238 and other essential auxiliaries (e.g., thin insulation film 232, unstretchable fabric 234 positioned underneath the thin insulation film 232 and electrodes 238, insulated conductive threads 242 and Faraday cage 236 positioned under the elastic band 240). A schematic, cross-sectional view of FIG. 18A is provided in FIG. 18B. The tissue water-content sensor 230 can be installed on the instrumented sock 8 like all the other sensors discussed herein.

Figure 18C:
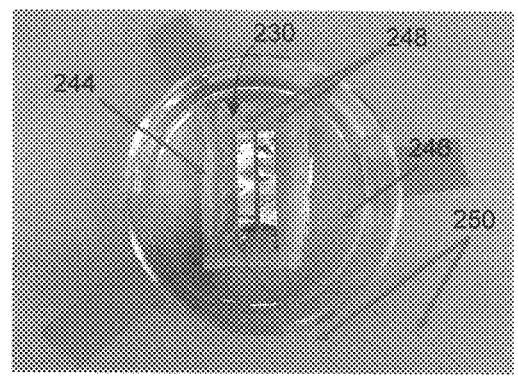
FIG. 18C is a photograph of an animal tissue test utilizing a conceptual equivalence of the water-content sensor of FIGS. 18A-18B.
Figure 18D:
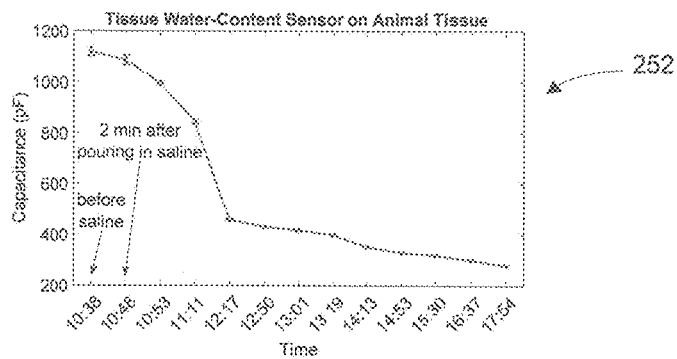
FIG. 18D is a graph illustrating the measured capacitance values by using water-content sensor on animal tissue.

As generally depicted in FIG. 18C, a preliminary test to verify the potential performance of the tissue water-content sensor 230, an animal tissue test was conducted as follows. First, a piece of clean and dry animal tissue was prepared. In this example, chicken animal tissue 244 was purchased from a local market. The tissue 244 was placed in a container and a conceptual equivalence of the tissue water-content sensor 230 was attached to the top side of the tissue 244. The tissue water-content sensor was connected to an L/C meter or a capacitance sensor IC chip (not shown) via wires 250. Physiological saline 246 was poured into the container until several millimeters away from the top side of the tissue 244. The top side of the tissue 244 was not soaked in the saline 246, since in real application of the tissue water-content sensor, the user's skin surface is usually dry and is not expected to have water in direct contact with the tissue water-content sensor. The chicken tissue 244 was left undisturbed, soaked in the saline 246, during which water from saline was slowly absorbed into the tissue 244. The L/C meter or the capacitance sensor IC chip's reading was recorded every hour or less. A graph 252 illustrating the results of this seven-hour long test is in FIG. 18D. The tissue water-content sensor 230 displays a monotonic trend as the water being slowly absorbed into the chicken tissue 244, which shows the potential for the disclosed tissue water-content sensor to work in real-world applications.

Various examples have been described. Any combination of the described operations or functions is contemplated. These and other embodiments are within the scope of the following claims.

Although the present disclosure has been described with reference to preferred embodiments, workers skilled in the art will recognize that changes can be made in form and detail without departing from the spirit and scope of the present disclosure.

What is claimed is:

1. A system for measuring a dimension of a sample, the system comprising:
   one or more magnetic sensors configured to detect a magnetic field;
   an electromagnet configured to produce the magnetic field detectable by one or more magnetic sensors;
   a controller module configured to control delivery of an alternating electrical signal to the electromagnet and receive, from each of the one or more magnetic sensors, a respective signal indicative of the magnetic field, the controller module further configured to average multiple peak-to-peak ranges measured by the one or more magnetic sensors as an indicator of the dimension of the sample; and
   a stretchable material, wherein the electromagnet and the one or more magnetic sensors are coupled to respective portions of the stretchable material.

2. The system of claim 1, wherein the controller module is configured to measure, based on the respective signal received from the one or more magnetic sensors, the dimension of the sample.

3. The system of claim 1, wherein the sample comprises a portion of a patient.

4. A system for measuring a status of physiological fluid accumulation of a patient, the system including a wearable material and a size measurement sensor configured for measuring the static size of a sample of the patient; wherein the sample is selected from the group consisting of a portion of a leg and a portion of an arm, further including an elasticity sensor configured to determine an elasticity of the sample, the elasticity sensor comprising:
   a first member comprising a first portion configured to deform a first area of the sample; a second member comprising a second portion configured to deform a second area of the sample different from the first area, wherein application of an external force to the first member causes the first portion to extend further into the sample than the second portion;
   a first force sensor coupled to the first member and configured to sense a first force to the first portion during deformation of the first area of the sample; and
   a second force sensor disposed between the first member and the second member and configured to sense a second force representative of contact between the first member and the second member when the second portion deforms the second area of the sample.

5. The system of claim 4, further including a heart rate sensor configured to measure changes to a heart-rate parameter of the sample.

6. The system of claim 4, further comprising a controller module configured to determine a progressive disease status of a physiological disease related to fluid accumulation, such as lymphedema, chronic venous insufficiency, heart failure, kidney failure, extremity trauma, based on at least one of a dimension variable measured using a respective signal indicative of a magnetic field, an elasticity variable measured from the tissue elasticity of the patient, a water content variable, and a heart rate variability measured from the patient.

7. The system of claim 4, further including a water-content sensor configured to measure changes to a water-content parameter of the sample; the water-content sensor selected from the group consisting of a bioelectrical capacitance sensor and a dielectric constant measurement sensor.

8. A device configured to determine an elasticity of a sample, the device comprising:
   a first member comprising a first portion configured to deform a first area of the sample;
   a second member comprising a second portion configured to deform a second area of the sample different from the first area, wherein application of an external force to the first member causes the first portion to extend further into the sample than the second portion;
   a first force sensor coupled to the first member and configured to sense a first force to the first portion during deformation of the first area of the sample;
   a second force sensor disposed between the first member and the second member and configured to sense a second force representative of contact between the first member and the second member when the second portion deforms the second area of the sample; and
   a controller module configured to detect, based on the first force and the second force, the elasticity of the sample.

9. The device of claim 8, further comprising a wearable material, wherein the first member, second member, first force sensor, second force sensor, and controller module are coupled to the wearable material.

10. The device of claim 8, wherein the sample comprises a portion of a patient.

11. A method for monitoring a physiological status of a patient, the method comprising:
   measuring, by a size sensor, changes to a size parameter of a limb of the patient:
   measuring, by an elasticity sensor, changes to an elasticity of a tissue portion of the patient;
   determining, by a processing module and based on at least one of the size parameter or the elasticity, a physiological parameter indicative of the physiological status;

determining, by the processing module, that the physiological parameter exceeds a threshold value; and transmitting, by a communication module, an alert signal to a computing device for alerting a user of the exceeded threshold value.

12. The method of claim 11, further comprising:

measuring, by a water-content sensor, changes to a water-content parameter of the patient; and measuring, by a heart-rate sensor, changes to a heart-rate parameter of the patient, wherein determining the physiological parameter comprises determining, based on at least one of the water-content parameter and the heart-rate parameter, the physiological parameter.

13. The method of claim 11, where the size sensor is configured to measure the static size of the limb.

14. The method of claim 11, the step of measuring, by a size sensor, utilizes an electromagnet continuously switched on and off.

15. The method of claim 14, wherein the electromagnet is alternatingly switched on an off every 300 milli-seconds.

* * * * *